United States Patent [19]

Sparks et al.

[11] Patent Number: 5,100,592
[45] Date of Patent: Mar. 31, 1992

[54] METHOD AND APPARATUS FOR GRANULATION AND GRANULATED PRODUCT

[75] Inventors: Robert E. Sparks, Kirkwood; Norbert Mason, Clayton; Michael Center, St. Louis, all of Mo.

[73] Assignee: Washington University Technology Associated, Inc., St. Louis, Mo.

[21] Appl. No.: 631,249

[22] Filed: Dec. 20, 1990

Related U.S. Application Data

[63] Continuation-in-part of Ser. No. 838,828, Mar. 12, 1986, Pat. No. 5,019,302.

[51] Int. Cl.$^5$ .......................... B29B 9/08; B29B 9/10
[52] U.S. Cl. ...................................... 264/7; 23/313 R; 264/8; 264/40.1; 264/40.7; 264/114; 264/117; 425/8; 425/145; 425/222
[58] Field of Search .................. 264/7, 8, 40.1, 40.7, 264/117, 114; 425/8, 145, 222, 332, 333; 23/313 R, 313 P

[56] References Cited

U.S. PATENT DOCUMENTS

| | | | |
|---|---|---|---|
| Re. 27,214 | 11/1971 | Nakahara | 264/15 |
| 1,915,201 | 6/1933 | Ragg | 425/8 |
| 2,818,601 | 1/1958 | Agarwal | 425/222 |
| 2,876,491 | 3/1959 | Meyer | 425/222 |
| 2,986,772 | 6/1961 | Patton, Jr. | 425/222 |
| 3,139,465 | 6/1964 | Klopf | |
| 3,295,838 | 1/1967 | Ban | 259/2 |
| 3,531,562 | 3/1969 | Serrano et al. | 264/117 |
| 3,743,464 | 7/1973 | Strobert | 425/222 |
| 3,966,975 | 6/1976 | Hansen et al. | 426/285 |
| 4,157,371 | 6/1979 | Paulson et al. | 264/114 |
| 4,174,937 | 11/1979 | Paulson et al. | 425/222 |
| 4,256,677 | 3/1981 | Lee | 264/8 |
| 4,310,483 | 1/1982 | Dörfel et al. | 264/117 |
| 4,341,759 | 7/1982 | Bogentoft et al. | |
| 4,374,074 | 2/1983 | Ueda et al. | 264/8 |

FOREIGN PATENT DOCUMENTS

1037792 of 1766 United Kingdom.

Primary Examiner—Mary Lynn Theisen
Attorney, Agent, or Firm—Fleit, Jacobson, Cohn, Price, Holman & Stern

[57] ABSTRACT

A method of melt granulation for powdery material is disclosed wherein the powdery material is discharged onto the upper surface of a heated rotary spreader for migration under centrifugal force to the periphery of the spreader accompanying by melting of a portion of the material and enrobing of non-melted particles by the melted material for discharge as enlarged granules from the periphery of the spreader. To improve the quality of the granules produced, the feed material is supplied to the spreader at two separate locations. The first location is the central portion of the spreader to provide the melted material and the second location is adjacent to the periphery of the spreader. The spreader is preferably in the form of a concave bowl or inverted truncated cone or dish. Feed material is supplied to the first location by a screw feeder extending down the side of the dish and at the second location by a rotary vaned distributor located within the dish which radially flings the feed material onto the inclined dish wall. The process and apparatus is particularly useful for the production of non-sticky granules which are difficult to form when a single central feed of material is used.

22 Claims, 7 Drawing Sheets

METHOD AND APPARATUS FOR GRANULATION AND GRANULATED PRODUCT

CROSS-REFERENCE TO BELATED APPLICATION

This application is a Continuation-in-part of application Ser. No. 06/838,828 filed Mar. 12, 1986 now U.S. Pat. No. 5,019,302. The content of the parent application is expressly incorporated herein in its entirety.

BACKGROUND OF THE INVENTION

1. Technical Field

The present invention is related to a method and apparatus for rapid granulation of particles, and to the resulting product. More particularly, the present invention is related to the formation of granules or particles of a larger size or mass of a desired range from a feed stock of smaller particles.

2. State of the Art

There are numerous techniques available for granulation of particles. A general review of current methods of granulation can be found in Chapter 7 of the "Handbook of Powder Science & Technology", edited by Fayed et al. and published in 1984 by Van Nostrand Reinhold Co., New York.

Agglomeration or granulation of smaller or finer particles into relatively larger or bigger sized masses is desirable for several reasons. For instance, when microencapsulation or coating of fine particles is necessary to control the release or interaction of these particles into or with the surrounding medium or environment, it may be advantageous to have these fine particles compacted or clustered into larger sized masses so as to reduce the total interacting surface area. In other situations, the material is available only in smaller particle size than could be tolerated or used in a particular application or could be readily handled for further processing, e.g., filling capsules with a pharmaceutically active material in difficult to handle fine powdered form as originally synthesized. Other reasons for granulation may be related to esthetics, rheology or safety, e.g., preventing dust explosions or inhalation of toxic or allergenic materials, ease of conveying, prevention of caking, increasing or decreasing bulk density, facilitating removal of solids from liquids or gases, separation of one kind of solid from another by size differential after processing, etc.

The methods or apparatus heretofore employed for granulation or agglomeration and clustering of fine particles such as powdered materials suffer from certain limitations or disadvantages. Some devices, for instance, tablet presses have a lower size limit (about ⅛ inch) and a limit on the production rate (several thousand pieces per minute). Roll pressing and extrusion requires expensive precision equipment subject to wear and tear. Equipment of this nature may also have a product size limitation similar to that of tablet presses. Agitation methods include pan mixers, paddle mixers, inclined discs, rotating drums and the like. These methods as used by the prior art often suffer from low production rates and have high space requirements. On the other hand, those processes which employ spray drying tend to be expensive due to high energy cost and are typically used to form granules below 100 microns in diameter. Prilling is generally limited to materials stable in molten form and to particles above 1 mm in diameter. Fluid bed granulation has high space requirements and the energy costs are also high.

Of special concern is the ability to granulate particles of materials which are easily decomposed or degraded, or which become sticky for a period of time after being melted and cooled. Many materials have both a decomposition temperature and a melting point. Particularly difficult to deal with are materials which decompose or are otherwise deleteriously affected by temperatures close to, or at, the melting point. In general, however, it has been found that such decomposition results not only from reaching a particular temperature, but also from being maintained at that temperature for a particular length of time which may vary greatly from one material to another. Many prior art granulation techniques fail to recognize this critical concept, resulting in the inability to granulate certain materials with conventionally available techniques because the materials are maintained at the undesirable temperature for an excessive period of time. Frequently, for example, feed materials will be melted in their entirety and then fed as a liquid to a rotating disk or the like for centrifugal dispersion as in spray cooling. The resultant product from such techniques may be totally unacceptable in that it is "sticky" or otherwise difficult to handle for further processing, or important characteristics of the starting material may be adversely affected by such treatment.

Thus, a need for an improved, efficiently simple and cost effective granulation process and apparatus, and particularly one that is sufficiently fast to be capable of handling especially thermally sensitive materials, is quite apparent. This need is at least to an extent, met by a process and apparatus as disclosed in the parent application which generally improves upon the prior art techniques described above.

Thus, in accordance with the invention disclosed in the parent application, a feed material is provided which contains a material to be granulated in fine particulate form, which material is capable of being partially or completely melted for a short period of time without deleterious effect, or a particulate material to be granulated admixed with a particulate, meltable binder. The feed material is deposited onto central portions of the surface of a spreader, at least portions of which are maintained at a temperature which is at or above the melting point of the meltable component in the feed material. The spreader has peripheral portions which are spaced from the central portions in normal operation and also has inclined side portions between the central and peripheral portions thereof. In practical terms, the spreader may be likened to a concave or truncated inverted cone rotating element such as a dish or bowl. In operation of the process, the feed material rapidly spreads substantially radially outwardly on the spreader by centrifugal force produced by its rotation and with at least a portion of the feed material having a velocity component in the direction of the surface of the spreader to maintain this portion of the feed material in contact with the heated surface of the spreader as it moves radially outwardly so that it is melted substantially solely by contact with the heated surface to form a layer of liquid from the melted portion of the feed material on the surface of the spreader. The rate of feed of the material and the energy input to the surface of the spreader is adjusted along with the rotational speed of the spreader so that there is sufficient time for at least partial melting of the meltable component of the feed material but insufficient time to deleteriously affect the material being granulated. The material being granulated, including the liquid component, is discharged from the peripheral portions of the spreader into an atmosphere cooler than the melting point of the meltable component so that granules are solidified in the cooler atmosphere into granules which are larger than the particle size of the feed material.

SUMMARY OF THE INVENTION

One of the problems encountered in prior art processes is that the resulting granulated products may become "sticky" or otherwise difficult to handle for further processing, or important characteristics of the starting material may be effectively decreased or destroyed by such treatments. It is an object of the present invention further to improve on the process and apparatus of the parent application, more particularly in this regard, by improving the control of the method and apparatus in reducing the tendency to produce "sticky" products, to make the method and apparatus generally more applicable to a wider range of products, and to enhance the process and apparatus by providing controls needed for higher production capacity.

Generally stated, the present invention improves upon the process and apparatus disclosed in the parent application by feeding material to be granulated onto the rotating spreader at two separate locations. A first supply of feed material is deposited on the rotating spreader substantially at the center thereof, as in the parent application, so that the material migrates outwardly across the spreader with a portion thereof being melted as previously if it is meltable or contains a meltable binding material. This fluid feed stream may be melted previously if it is stable at above its melting temperature, or it may be a solution or suspension, in which case the heat for melting is not required. A second supply of fine particulate feed material is deposited onto the migrating first supply at a location intermediate between the central portion and the peripheral portion of the spreader so as to mix with the first supply of material, with less susceptibility to melting, due to decreased residence time on the spreader, while still providing a sufficient period for particle granules from the second supply of material to become at least partly wetted with melted material or solution of the first supply.

In a preferred form of the invention, the second supply of material is flung onto the spreader in a circular band, for example from a centrally located rotating flinger means such as a vaned disk assembly. The first supply of material may be deposited onto the center of the spreader from a conveyor tube, a hollow shaft from below if it is a liquid or if the stream is composed of fine solid particles, or the like extending radially into the spreader from the periphery thereof, the tube being located above the active surface of the spreader.

In all other respects the method and apparatus according to the invention may be substantially similar to the method and apparatus as disclosed in the parent application.

BRIEF DESCRIPTION OF DRAWINGS

FIG. 1 is a somewhat diagrammatic sectional side elevational view of granulation apparatus in accordance with the invention;

FIG. 2 is an enlarged part sectional view of a rotary feed distributor used in the apparatus;

FIG. 3 is a sectional view on line 3—3 of FIG. 2,

FIGS. 4*a*–4*d* are diagrammatic views of differently shaped spreader means for use in the invention;

FIGS. 5*a*–5*d* are diagrammatic views of differently shaped rotary distributors;

FIG. 6*a* is a partly diagrammatic side elevational view of the apparatus shown in FIG. 1 being used for coating core particles with a covering layers incorporating fine particles;

FIG. 6*b* shows core particles coated with a wall containing fine particles.

FIG. 7 is a diagrammatic view similar to FIG. 1 of a modified form of the apparatus in accordance with the invention;

FIGS. 8*a* and 8*b* are diagrammatic views of further modified forms of the apparatus, and wherein the coating consists of a suspension or emulsion;

FIGS. 9*a* and 9*b* are diagrammatic views showing effects obtained using differently shaped spreader means and different gaps between the vaned distributor and the spreader.

FIG. 10 is a diagrammatic view showing still another modified form of the apparatus incorporating multiple spreader surfaces.

DESCRIPTION OF PREFERRED EMBODIMENT

Referring initially to FIG. 1, there is illustrated therein granulation apparatus according to the invention which, in general terms, is similar to that disclosed in the parent application.

Thus, the illustrated apparatus includes a rotary spreader means 10 generally in the form of a concave dish or bowl having a substantially flat central portion 10*a* and an inclined side wall lob extending from the central portion to the outer peripheral portion 10*c* of the spreader means. The spreader means is carried by a vertical shaft 12 and may be rotated by a conventional electric DC or other motor 14 having a suitable speed control, as in the parent application, and not shown herein.

In order to control the temperature and general ambiance within the spreader means and particularly on the upper concave surface thereof, the spreader means is provided with a lower heated shroud 16 in the form of a cylindrical chamber and a substantially flat disk-like upper shroud 18. The lower shroud 16 may be heated, for example by an electric heating jacket 20 and/or by hot air heating ducts 22 which may circulate hot air in the chamber through air passages 24 formed in its base wall.

The above described heating means is intended to control the temperature on the upper surface of the rotary spreader means 10 in the manner described in the parent application for the purpose of rapidly melting feed material fed onto the spreader means as will be described. Thus, in this regard, the heating controls may generally be similar to those described in the parent application and a temperature sensing device 26 or the like may be provided within the lower shroud.

In accordance with the present invention, two separate supply systems are provided for introducing powdered material for granulation onto the upper surface of the spreader means 10. A first supply of powdered material may be deposited substantially centrally on the spreader means through a screw feeder or like device 30 having a hopper 32 and feed screw 34 rotated by a motor 36 or the like. The feed device 30 may itself be supplied from a similar auxiliary feeder 40 which supplies material to the hopper 32 as required. The feed device 30 angles down one side of the spreader means 10 with a spacing there-between. If the first feed stream is a fluid it may be fed from below through a hollow shaft (as described in more detail below), or through a tube oriented down the side of the spreader means similar in position to feed device 30 in FIG. 3.

A second supply of powdered feed material is introduced onto the spreader means at a location substantially closer to the outer peripheral portion 10c through a rotary vaned distributor generally indicated by reference 50. The distributor 50 depends into the spreader means 10 from a suitable support (not shown) and serves to distribute the second supply of feed material from a hopper 52 through feed pipes 54 and 56. The vaned rotary distributor 50 is carried on the bottom of a shaft 58 rotated by a motor 60. Again, hopper 52 may be supplied with feed material from an auxiliary screw feeder 62.

Figures 1, 2, 3:
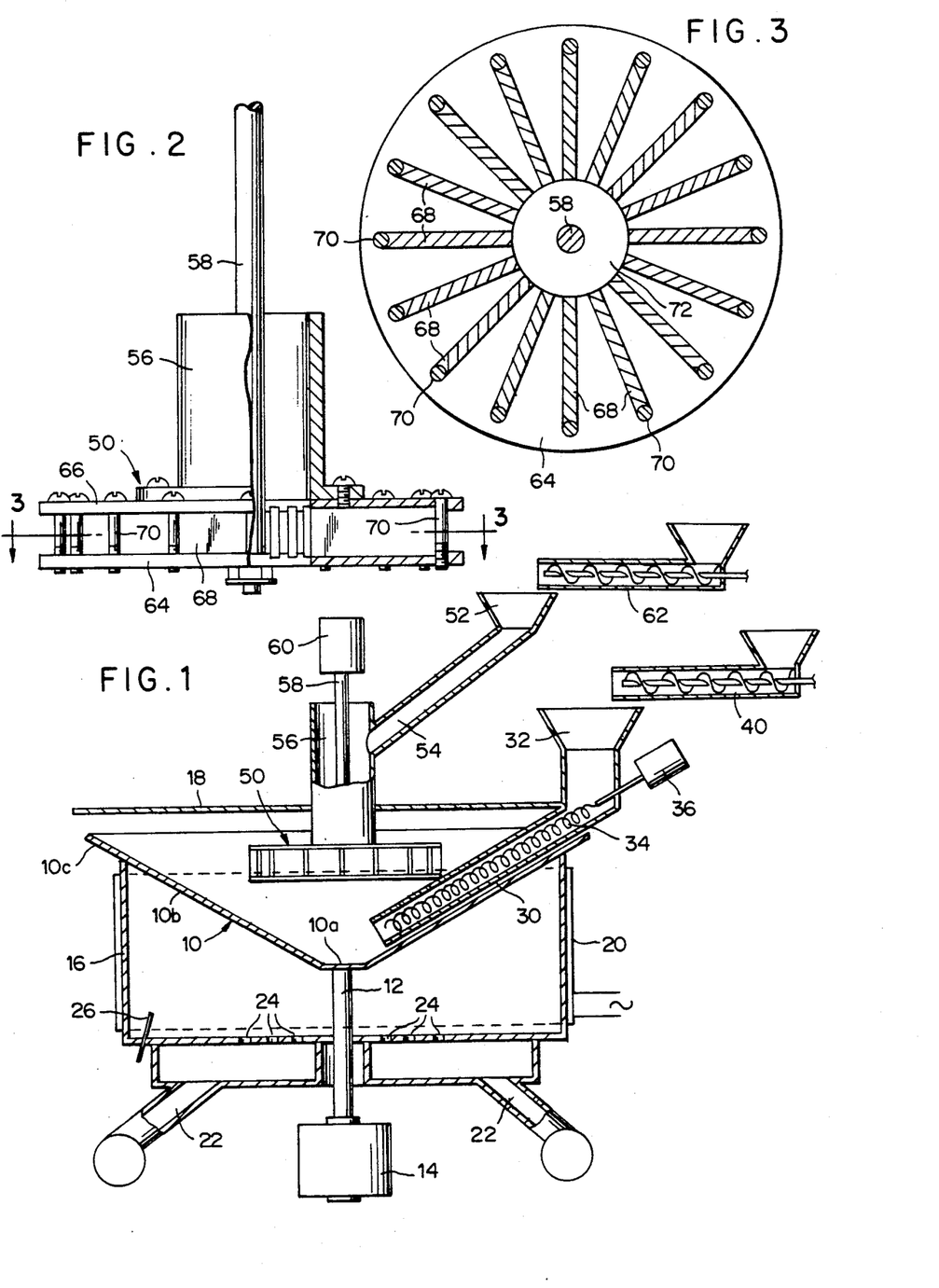

The structure of the rotary distributor 50 is shown in more detail in FIGS. 2 and 3 where it is evident that the distributor comprises a vaned disk-type arrangement having a pair of spaced parallel disks 64 and 66 with radial vanes 68 there between, the assembly being held together by a series of screws 70. The vanes 68 are spaced from shaft 58 to provide a central supply space 72 for material received from the tube 56. Speed controls (not shown) of known type may be provided for the motor 60 and the effect of rotation of the distributor 50 is to fling the second supply of feed material substantially radially outwardly in a horizontal plane against the inner surface of the film from the first feed stream on the spreader means 10 at a radial location between the central portion 10a and the peripheral portion 10c. If the first feed stream is meltable, the powder from the second feed stream should impinge upon the melted, or partially melted first feed stream.

As in the parent application, heating of the spreader means 10 causes the first supply of feed material received from the feeder 30 substantially centrally of the spreader means 10 to be melted as the material migrates from the central portion 10a toward the peripheral portion 10c of the spreader means 10 through centrifugal force, thus forming a film on the spreader means 10. By contrast, the feed material received from the distributor 50 has a significantly reduced residence time on the spreader means 10 so that melting of this material is significantly less and the overall effect is to deposit the particles received from distributor 50 onto the film of melted material migrating up the spreader means 10. In general terms, substantially equal quantities of the feed material may be provided through the separate supply systems, or the ratio of the feed streams may be controlled independently by separate feed controls.

It is evident that the precise location at which material from the rotary distributor 50 encounters the spreader means 10 will be dependent on the relative vertical position of the rotary vaned distributor 50, its diameter and its speed of rotation. Increases in such rotation cause the flung material to more closely be distributed in a horizontal plane.

The two stage feeding of material to the spreader means 10 is particularly useful for substances which may tend to produce "sticky" granules due to slow recrystallization as described more fully in the parent application.

If a material is known to decompose above its melting point or recrystallizes only with difficulty if heated above its melting point (such as many sugars do) the location of the vaned distributor 50 may be critical and should be chosen to discharge the second feed stream at a height on the spreader means 10 where all the solids being fed from below have just melted. This may be ascertained experimentally with an infrared thermometer. In other cases this location may not be critical.

In critical cases it is also beneficial to make the clearance between the rim of the vaned distributor 50 and the spreader means 10 rather narrow to insure that fine feeds reach the film of the first feed stream and do not become airborne and be directed elsewhere on the film or build up on the cover of the machinery.

In one particular example showing the benefits of the present invention, apparatus which did not produce dry, non-sticky beads of metoprolol succinate (MPS) when operated as in Example 4 of the parent application was equipped with a vaned distributor 50 which was used to throw finely ground crystals of MPS on the thin melted liquid film as it migrated upward on the rotating bowl of the spreader means 10. This change produced nonsticky beads. The feed rate of the finely ground crystals fed through the vaned distributor was approximately the same as the rate of crystals fed to the center of the bowl with the feed screw 34. This shows that with Type 2B and Type 2C substances as referred to in the parent application, the sensitivity to temperature profile on the spreader means 10 can be reduced by feeding finely ground crystals close to the edge. This experiment is detailed in Example 1 appended below.

Furthermore the invention is able to avoid discoloration of acetaminophen (Paracetamol) which as stated in Example 8 of the parent application has 10% beads with a brown tinge, which are therefore not useful. Among new substances which can be successfully melt granulated are sulfamethazine (Sulfadimidine) Type 1A, and phenylephrine hydrochloride, Type 2B. Another substance, Chlorpheniramine maleate, formed non-sticky spheres in melt granulation but each sphere then fractured into several pieces. Slower cooling in an annealing tower may prevent this. Chlorpheniramine maleate is the only substance which did this showing that the melt granulation is of general utility.

To granulate acetaminophen without discoloration, the spreader means 10 was speeded up to nearly 3,000 RPM and the spreader means 10 temperature simultaneously increased. The bead size decreased to the range of 100 to 200 microns. The shorter contact time with the hot surface eliminated discoloration.

Spheres have been made from approximately 100 microns in diameter to about 600 micron. The 100 micron beads were made with an 11 inch diameter 20 degree bowl rotated at about 3,000 RPM. The 600 micron beads were made at 900 RPM.

There is a speed which depends on viscosity, below which the bowl does not throw droplets anymore but big chunks. For relatively viscous substances it is near 700 RPM for a 8 inch diameter bowl and would correspond to 700 to 800 micron. For less viscous substances the limiting bowl speed is lower, although the droplet sizes would not be larger.

At high bowl speeds particles smaller than 100 micron can be made. Under ideal conditions particles as small as 10 micron might be made. The major problem is heat transfer. The contact time between particle and spreader means surface decreases and heat losses to the air increase with increasing bowl speed.

As the size of a feed particle increases the amount of heat which needs to be transferred in order to melt it, increases more rapidly than the spreader means surface contact area through which it must be transferred. Therefore smaller particles melt more readily on the spreader means surface. It has been beneficial to grind or otherwise subdivide the solid feed to well below the size of the desired spherical granular product. Besides improving the efficiency of melting it also improves the separation between any unconverted feed particles and the granular product. Many substances have been encountered which had crystals larger than the granules desired. Hence, it was necessary to grind the feed to permit separating the product by sieving.

If the feed particle size of the second stream is substantially larger than the thickness of the liquid film on the spreader means from the first feed stream and conditions are such that the solid does not melt, it will likely be coated as a single particle with the liquid, in accordance with U.S. Pat. No. 4,675,140 rather than be granulated into a much larger particle by agglomeration with other solid particles.

The second feed stream of fine solids may also be used to add nonmelting solids to the film on the disk. Due to the extremely short contact time on the rotating spreader means, highly labile fine solids may be added to or granulated with the liquid stream. This would permit granulation or inclusion of e.g. cells, enzymes and thermally labile molecules.

The second feed stream of fine solids may also consist of material which is soluble in or melted by the liquid film. In this case the contact time on the spreader means is so short that the solids cannot be dissolved or completely wetted while on the spreader means disk, but behave as if they were inert partly wetted solids. This permits the formation of unique particles. For example, the liquid film may be a slurry of fine particles of KCL in a saturated KCL solution such that the viscosity of the stream is much higher than water e.g. similar to the viscosity of a heavy cream. If an additional 20% of fine KCL were added to this stream in the bulk, the stream would become a non fluid paste. However, if the additional KCL is added as the second solid feed stream in the present invention, the fine solids will only have time to be partially wetted by the fluid. Therefore the thin film viscosity will not be appreciably increased by the fine solids in this very short period of time. The fluid stream will exit the spreader means the fine solids sitting on the surface, droplets will form containing the fine solids, which will then be completely wetted, in some cases setting the droplets as semisolid paste. Hence, droplets have been formed of material which, in equilibrium wetting, will not flow to form droplets.

The present invention can also give improvements in the process of melt granulation. In the usual process, a slurry of fine solids in a melted binder are atomized and the droplets cooled to give a solid matrix containing the suspended fine solids. The limit in solid content is set by the maximum viscosity of the slurry which can be properly atomized. This is often 20-35% solids by volume. In the present invention, such a slurry can be fed to the spreader means as the first feed stream, spreading out into a film.

However, additional fine solids are added to the top of the film from the second feed stream, e.g. from the rotating vaned distributor 50. Since there is insufficient time on the spreader means for complete wetting of the solids from the second feed stream, the particles from this stream will be sitting on the film as it exits the spreader means forming droplets. In the droplet formation, the liquid slurry will envelop the solids which will then become wetted. The droplets will be solidified, giving a product with a higher solids content than could be formed by usual melt-granulation. This greatly extends the range of solid content which can be obtained using an expensive melted binder.

If the first stream is a melt, solution, suspension or emulsion, one advantage stems from the speed with which solids can be added to the liquid stream just before droplet formation. There is not sufficient time for the solids to be completely wetted (just as in the case where solids in the first stream cannot be totally melted). Hence, the partially wetted solids are included in the droplets formed. Subsequently they wet and the viscosity of the droplet may increase substantially. It may be sufficiently solid to permit handling, subsequent drying or coating operations, and the like. If all or a portion of the solids added in the second feed stream can cause a gelation or large increase in viscosity when dissolved, then the viscosity of the fluid in the droplet will increase greatly after formation containing the fine solids. For example, if the fine solids in the second stream are finely divided gelatin and the liquid film is an aqueous solution, dispersion or emulsion, the droplets will form before the gelatin can dissolve. However, while the droplet is falling through air, the gelatin will begin to dissolve, then will gel upon cooling. Within seconds the droplet will be solid enough for subsequent handling. Solids in the second stream may be meltable or non-meltable soluble or non-soluble.

The spreader means, for dispersion of fine solids, may be flat, vaned, bowl-shaped, a turbine, stepped, sharp-edged or any other variation in shape which will provide the required even distribution of the solids onto the surface of the fluid film on the spreader means.

Figure 4A:
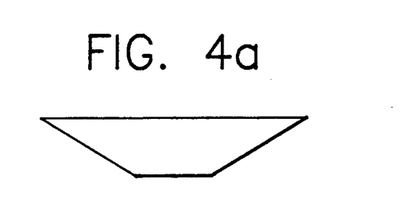
Figure 4B:
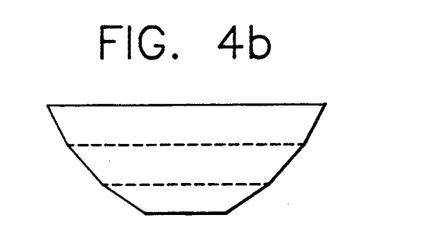
Figure 4C:
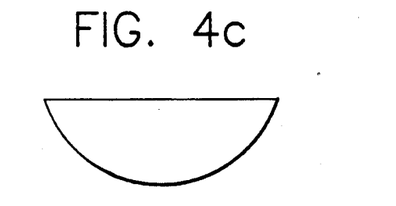
Figure 4D:
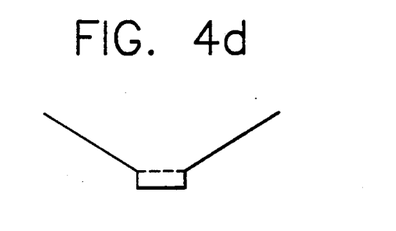

The spreader means may be modified in shape to provide for better or longer contact of the second-stream film solids with the liquid film. For example the angle with the horizontal may be increased to give better contact. Thus, examples of differently shaped spreader means are shown in FIGS. 4a-4d. FIG. 4a shows a simple angled disk as the spreader means, FIG. 4b shows a multi-angled disk, FIG. 4c shows a concave disk and FIG. 4d shows an angled disk with a central cup.

Figure 5A:
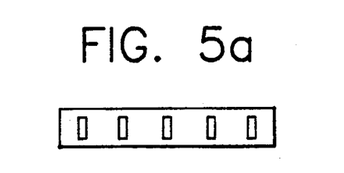
Figure 5B:
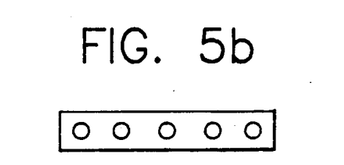
Figure 5C:
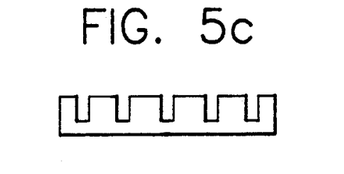
Figure 5D:
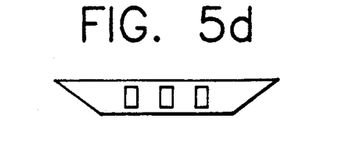

Different rotary distributor configurations are shown diagrammatically in FIGS. 5a-5d. Thus, FIG. 5a shows a vaned distributor, FIG. 5b shows a distributor with tube-shaped vanes, FIG. 5c shows a crenated distributor, and FIG. 5d shows a distributor having an angled profile to conform with the profile of the spreader means.

Figures 6A, 6B:
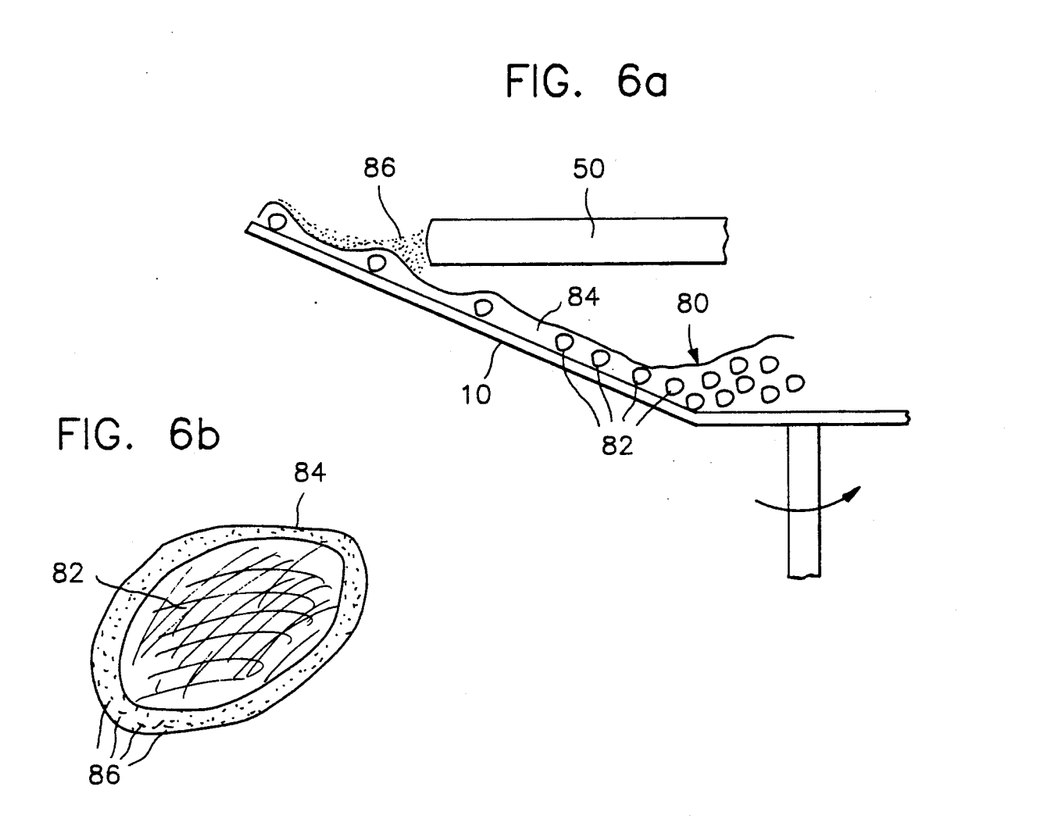
Figure 7:
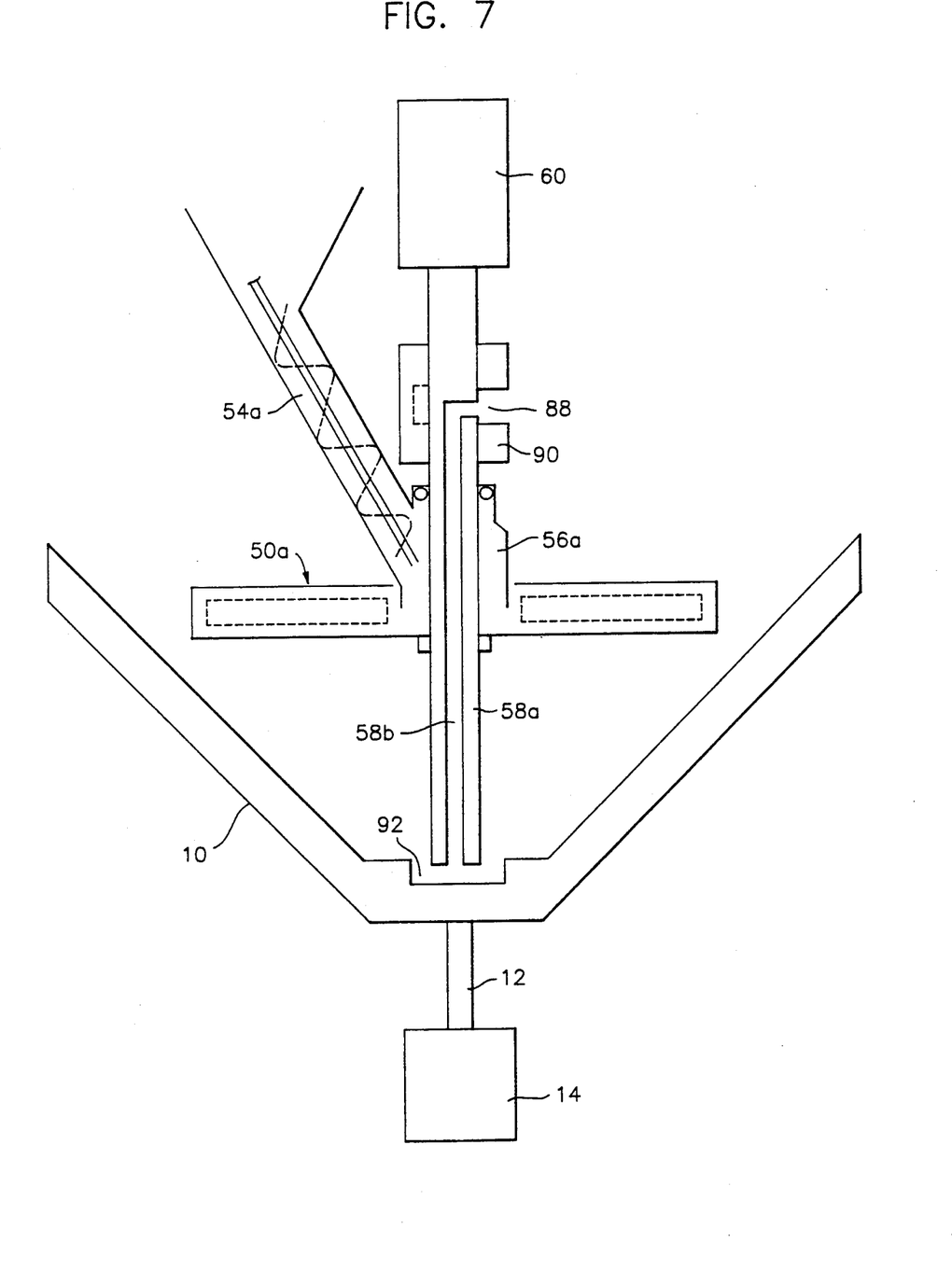
Figure 8A:
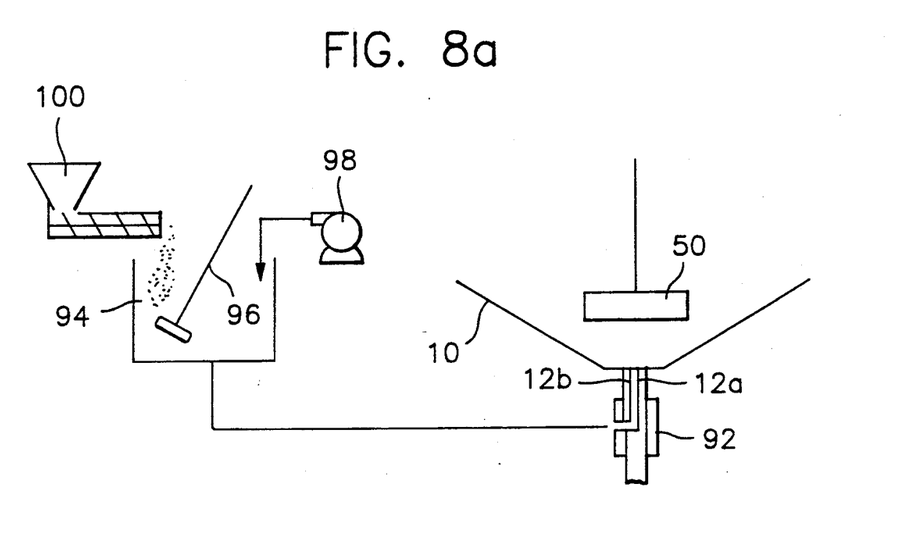
Figure 8B:
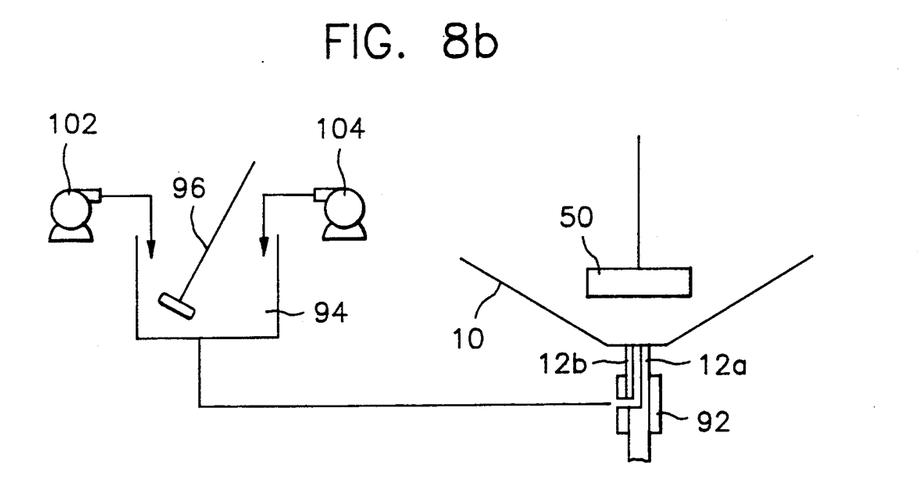
Figure 9A:
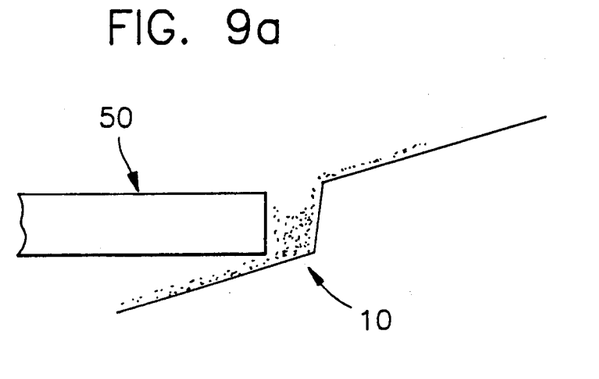
Figure 9B:
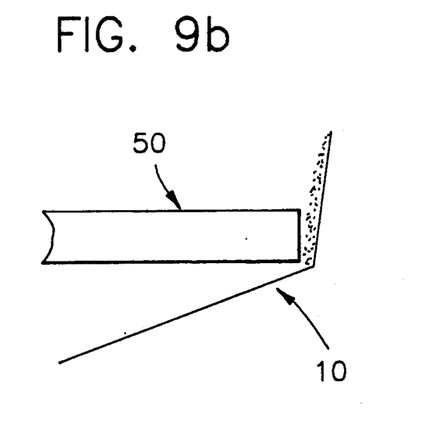
Figure 10:
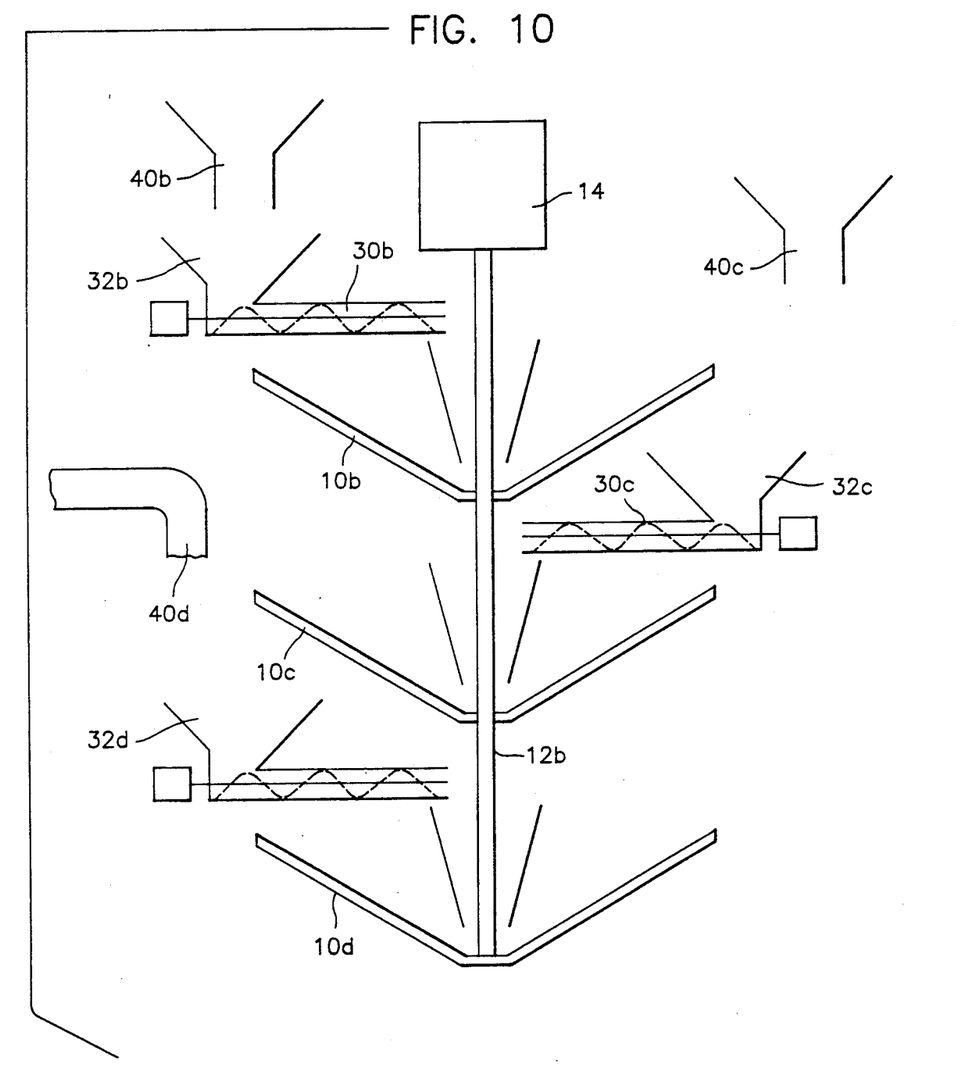

The present invention can also be used for placing solids in a coating of a larger core particle as a modification of the invention disclosed in the aforenoted U.S. Patent. Thus, as shown in FIG. 6a, a feed suspension 80 of core particles 82 in a coating liquid 84 may be fed, as previously described, to the center of spreader means 10, as the first stream, and fine solids 86 from distributor 50 may be fed to the spreader means as the second stream. The resulting product flung from the spreader means, as shown enlarged in FIG. 6b will have the core particles 82 embedded in a solidified coating of the liquid 84 with included fine particles 86.

The position of the vaned distributor or rotor relative to the surface of the spreader means is determined in part by the particle size of the solids to be fed by the vaned rotor. If the particles are very small, the rotor periphery should be very close to the surface of the spreader because fine particles do not have much momentum imparted to them by the rotor because of their small mass hence are subject to being blown about by air currents, e.g. for particles 10 to 100 micron the gap should not be greater than ⅛ in. (3 mm) preferably smaller. It may be beneficial to have the periphery conform to the shape of the spreader, as shown in FIG. 5*a* i.e., if the spreader is angled the rotor edge should be slanted to follow the same angle. If, on the other hand, large particles are to be fed which only need to touch the liquid briefly, then larger gaps should be considered, e.g. to contact larger metal particles with small amounts of lubricants.

If it is desired to granulate a substance which decomposes above its melting point and the production rate must be maximized the vaned rotor should feed the fine crystals at a distance from the center of the spreader where the temperature just reaches the melting point. This may be determined experimentally by the use of an infrared thermometer. From that point on they should be distributed all the way to the periphery of the spreader. This application would require a relatively small vaned rotor and the gap between rotor and spreader is not so critical.

It is possible for large heavy particles to bounce on the spreader thus to have poor contact with the liquid. There are at least three measures which can be taken to lessen this effect. 1) to decrease the speed of the vaned rotor, 2) to increase the angle on the spreader (the bouncing phenomenon is worst on a flat disc least on a disc of maximum angle i.e. 60 degrees), 3) to increase the viscosity of the liquid phase.

As shown in FIG. 7, the first stream, when in the form of a liquid, slurry or emulsion may be fed to the spreader means through the shaft 58*a* of the rotary distributor 50*a*. The shaft has a central bore 58 for receiving the liquid from an annular port 88 in a seal assembly 90 which does not rotate.

The second supply material is fed from a hopper with screw feeder 54*a* to the annular space of the vaned rotor driven by the central shaft through its bottom surface. The vaned rotor has a slot through the top surface through which it receives the solids. There is a depression 92 in the spreader of larger diameter than the shaft. This helps to obtain a better distribution of the liquid stream.

FIGS. 8*a*, and 8*b* show diagrammatically arrangements whereby the first supply of material may be fed upwardly to the spreader means 10 through a hollow shaft 12*a* which replaces shaft 12 of the first embodiment. Shaft 12*a* has a central bore 12*b* which opens into the center of the spreader means and receives the first material, in the form of a liquid, slurry or emulsion through a stationary seal assembly 92 similar to assembly 90 as shown in FIG. 7. The material is received from a holding tank 94 with a mixer 96. FIG. 8*a* shows an arrangement where the material comprises solids suspended in a coating liquid, the solids being supplied to tank 94 by a screw feeder 100 and the coating liquid through a pump 98. FIG. 8*b* shows an arrangement where the material is an emulsion of two liquids supplied to tank 94 through respective pumps 102 and 104.

Besides the preparation of suspensions and emulsions shown in the Figures, emulsions or suspension can be also preexisting such as latexes or pseudolatexes solutions or pastes, provided they can be made to flow by a pump.

As shown in FIGS. 9*a* and 9*b*, in the neighborhood of the vaned distributor, the slope of the angle of the spreader may be increased say from 20 degrees to 60 degrees. Once past this region it can again go to 20 degrees (FIG. 9*a*) or could continue at 60 degrees with the horizontal (FIG. 9*b*). This would be beneficial where the powder must have a certain contact time to react with the liquid before it is cooled or quenched.

In accordance with another aspect of the invention shown in FIG. 10, a plurality of stacked spreaders 10*b*–10*d* may be provided on a common shaft 12*b* each spreader being used for granulating a single supply of material as in the parent application. Stacked spreaders can be important in melt granulation when very uniform particles are desired. Increased feed rates on a single spreader may lead to a broader size distribution. Stacked spreaders allow higher production of uniform particles. In pharmaceutical applications to have very uniform drug particles can be of benefit because the bioavailability as well as the release rate is more predictable.

Stacked spreaders can also be important in melt granulation when production is limited by the heat transfer rate on the spreader. The heat of melting must be transferred to the particle in the short time it resides on the spreader this could limit the production rate since the spreader temperature has an upper limit. Production rate can then be increased by stacking of the spreader means. It is also contemplated that stacked spreaders may be useful for performing granulation with first and second material supplies (as previously described) on one or more of the spreaders.

Hoppers 32*b*–32*d* to the respective screw feeders 30*b*–30*d* are filled at intervals from chutes 40*b*–40*d* from above. In melt granulation each spreader is heated separately, e.g. by induction heating, the coils being installed immediately below the spreader.

EXAMPLE 1

Effect of Seed Crystals

The arrangement was as in FIG. 1. An 11 inch diameter 20 degree bowl pressed from sheet aluminum which previously had made only sticky metoprolol succinate beads was equipped with the two feeders, one which fed solids to near the center of the bowl through a tube inclined parallel to the surface of the bowl but approximately ¼ to ⅜ inch above the bowl surface. The second feeder fed a small vaned disc which was designed to throw finely divided crystals higher up on the bowl surface. The vaned disc was 4 inches in diameter ⅜ inch total height. It was positioned so that its top surface was only slightly lower than the top surface of the 11 inch bowl. Therefore its bottom surface was 1⅛ inch above the bottom of the bowl, the bowl being a 20 inverted cone except for a 2 inch diameter flat portion in its center. The vane disc rotated at 600 RPM. The granulation appeared to work better when the vane and bowl went in the same direction. The placement in the particular example was dictated by the geometry of the parts since it was necessary to have room for the feed pipe to the center of the bowl. The bowl rotated at 1,000 RPM and was heated to approximately 180° C. The drug was fed at 1.2 kg/hr to the center of the disc and 1.2 kg/hr through vaned distributor. Non-sticky spheres near 250 microns in diameter were produced.

EXAMPLE 2

Granulation of Acetaminophen

Powdered Acetaminophen was granulated using the same 11 inch bowl as in Example 1., but the disk was driven at 2,950 RPM with a belt drive. Acetaminophen is so thermally unstable that few seconds at its melting point causes an undesirable darkening. The drug was fed through a concentric space around the central shaft. Only one feed stream was found to be necessary. A cover which was parallel to the surface of the bowl was fastened to the concentric feed pipe around the axis. The cover was ⅛ to ¼ inch away from the bowl surface and was designed to keep the solids close to the bowl surface to increase the efficiency of the melting process. The granular spheres were white and 100 to 120 micron in diameter.

EXAMPLE 3

Granulation of a Herbicide

This granulation depended on the melting of one of the ingredients to bind loose powder into granules. The mixture was as follows: pendimethalin, (prowl ®, micronized. 100 gm), corn starch 45 gm, powdered sugar 45 gm, tamol 10 gm. Disc temperature was 107° to 117° C., disc speed 750 RPM. These granules were not round but were fluffy and of arbitrary shape.

EXAMPLE 4

Granulation of Sulfamethazine (Sulphadimidine).

An 11 inch bowl was used and the cover on the bowl was parallel to its top surface and close to it. Temperature measured below the bowl was 250° C. Three runs were made in succession in which the bowl speed was 900, 1,200, and 1,700 RPM. With the 900 RPM Run 86.5% of the product was between 417 and 590 micron, with the 1,200 RPM Run 72% of the product was between 300 and 417 micron and with the 1,700 RPM Run 79.2% of the product was between 88 and 300 micron. These distributions were obtained by sieving. Micrographs showed extremely uniform spherical beads.

EXAMPLE 5

Granulation of Phenylephrine Hydrochloride.

The bowl was 11 inch in diameter and the cover was parallel to the top surface of the disc and close to it. The temperature below the disc was 150° C. The speed of rotation was 2,750 RPM. The beads were 200 micron in diameter. They were slightly sticky at first but were easily recovered.

EXAMPLE 6

Granulation of Benzoic and P-Aminobenzoic Acids.

The apparatus was similar to that in Example 4 in the parent application except a liquid feed tube was added concentrically to the solids feeder. A 6 mm copper tube was bent into a circle approximately 4 inches in diameter and 6.5 mm holes were drilled at regular intervals. The inlet of the tube was connected to a pump. The tube entered through the cover and was mounted concentrically with the solids feeder tube.

To granulate p-amino benzoic acid (paba), solid paba was fed through the solids feeder and a solution of 10 gm paba per 100 ml ethanol was fed to the liquid distributor. The disc speed was set to 1,200 RPM, the dry feeder was rotated at 20 RPM, the liquid pumping rate was 8.6 ml/min. The temperature of the disc was 65° C. Conversion per pass to beads larger than 250 micron was approximately 6%. The beads were of relatively low strength.

To granulate benzoic acid a solution of 40 gm benzoic acid per 100 ml ethanol was used. Instead of circular distributor for the liquid, four tubes spaced 90 degrees from each other were used equidistant from the central solids feeder. Each of the tubes were connected to a pump. The disc speed and the solids feed rate were the same as the paba but the liquid rate was 0.82 ml per minute to each tube for a total of 3.3 ml per minute. Conversion to granules (150 to 600 micron) was 7% when benzoic acid was used as received and 9.5% when it was ground. In contrast to paba benzoic acid the granulated benzoic arid contained approximately 20% particles greater than 600 microns in diameter. Such particles can be broken and recycled if it is desired to produce only particles smaller than 600 micron. The benzoic acid particles were stronger than the paba particles.

What we claim is:

1. In a process for the granulation of a powdery material wherein the material is discharged onto a surface of a heated rotary spreader means for migration across the surface by centrifugal force from an inner region of the surface toward a peripheral region of the surface accompanied by partial or total melting of the material and enrobing of nonmelted particles by melted material for discharge thereof from the peripheral portion of the surface as discreet granules, the improvement which comprises feeding the material onto the surface of the spreader means at first and second locations which are respectively closer to and further from the center of rotation of the spreader means.

2. The invention defined in claim 1 wherein the quantities of powdery material fed to the disc are substantially equal at the respective first and second locations.

3. The invention defined in claim 1 wherein the first location is substantially at the center of the rotation of the spreader means and the second location is adjacent the periphery of the spreader means.

4. The invention defined in claim 1 wherein the said surface of the spreader means is substantially concave.

5. The invention defined in claim 4 wherein said first location is substantially at the center of rotation of the spreader means and the second location is adjacent the periphery of the spreader means.

6. The invention as defined in claim 4 wherein the powdery material is radially flung onto said surface of the spreader means at said second location from a rotary distributor located within the spreader means.

7. The invention defined in claim 6 wherein the speed of rotation of the distributor is controlled so as to control the position of said second location on said surface of the spreader means.

8. The invention as defined in claim 6 wherein the powdery material is fed onto said surface of the spreader means by gravity at said first location.

9. The invention defined in claim 8 wherein the spreader means is a inverted cone or concave bowl and wherein the feed material is fed onto said surface of the spreader means at said first location by a mechanical feeder extending substantially to the center of the bowl from the periphery thereof and spaced above said surface of the spreader means.

10. The invention defined in claim 1 wherein the spreader is an inverted cone or concave bowl carried atop a hollow rotary shaft, and wherein the feed material contained in a liquid is fed onto said surface at said first location by upward passage of the liquid through said shaft.

11. Apparatus for melt granulation of a powdery material comprising a spreader means having an upper surface for receiving feed material to be granulated, means for rotating the spreader means about an axis of rotation, means for heating said surface of the spreader means so as to at least partially melt powdery material deposited on said surface as the material migrates under centrifugal force toward a peripheral portion of the spreader means, first feed means for depositing material on the spreader means at a first location and second feed means for depositing material on said surface of the spreader means at a second location which is closer to the periphery of the spreader means than said first location wherein the first feed means is located for supplying material substantially to a central portion of the spreader means and the second feed means is located for supplying material to a portion of the spreader means adjacent to the periphery thereof and wherein the second feed means comprises a rotary distributor located within the spreader means for radially flinging the powdery material onto said surface of the spreader means at said second location.

12. The invention defined in claim 11 wherein said surface of the spreader means is substantially concave.

13. The invention defined in claim 12 wherein said surface of the spreader means has a substantially flat central portion and an inclined portion extending from the central portion to the periphery of the spreader means.

14. The invention as defined in claim 11 which includes means for controlling the speed of rotation of the rotary distributor thereby controlling the precise position of said second location.

15. Apparatus for melt granulation of a powdery material comprising a spreader means having an upper surface for receiving feed material to be granulated, means for rotating the spreader means about an axis of rotation, means for heating said surface of the spreader means so as to at least partially melt powdery material deposited on said surface as the material migrates under centrifugal force toward a peripheral portion of the spreader means, first feed means for depositing material on the spreader means at a first location and second feed means for depositing material on said surface of the spreader means at a second location which is closer to the periphery of the spreader means than said first location wherein the first feed means is located for supplying material substantially to a central portion of the spreader means and the second feed means is located for supplying material to a portion of the spreader means adjacent to the periphery thereof and wherein the first feed means includes a feeder extending substantially above said surface of the spreader means from the periphery thereof substantially to the central portion of the spreader means for depositing material at said first location.

16. The invention as defined in claim 15 wherein said feeder is a screw feeder.

17. Apparatus for melt granulation of a powdery material comprising a spreader means having an upper surface for receiving feed material to be granulated, means for rotating the spreader means about an axis of rotation, means for heating said surface of the spreader means so as to at least partially melt powdery material deposited on said surface as the material migrates under centrifugal force toward a peripheral portion of the spreader means, first feed means for depositing material on the spreader means at a first location and second feed means for depositing material on said surface of the spreader means at a second location which is closer to the periphery of the spreader means than said first location wherein the spreader means is carried atop a hollow rotary shaft and wherein the first feed means comprises means for supplying material contained in a liquid substantially to the center of said surface through said hollow shaft.

18. The invention as defined in claim 11 wherein the rotary distributor is suspended on a hollow shaft and the second feed means comprises means for supplying material contained in a liquid to the distributor through said hollow shaft.

19. Apparatus for melt granulation of a powdery material comprising at least two superposed rotary spreader elements each having an upper surface for receiving material to be granulated, means for rotating the spreader elements, means for heating the surfaces of the respective spreader elements, and feed means for each spreader element for feeding material onto the respective surface of the spreader element for migration of the material under centrifugal force toward the periphery of the element accompanied by melt granulation of the material.

20. The invention of claim 19 wherein the spreader elements are mounted for rotation about a common rotation axis.

21. The invention of claim 20 wherein the spreader elements are mounted for rotation a common shaft.

22. The invention of claim 19 wherein each spreader element is substantially bowl-shaped and the feed means is positioned for delivering material substantially to a central portion of the respective element.

* * * * *